(12) United States Patent
Hanai et al.

(10) Patent No.: US 9,140,462 B2
(45) Date of Patent: Sep. 22, 2015

(54) CHARGED PARTICLE EMISSION DEVICE AND AIR-BLOWING DEVICE

(71) Applicant: Sharp Kabushiki Kaisha, Osaka-shi, Osaka (JP)

(72) Inventors: Takahiro Hanai, Osaka (JP); Kenichi Shiraishi, Osaka (JP); Nobuhiro Iwaki, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/402,784

(22) PCT Filed: May 23, 2013

(86) PCT No.: PCT/JP2013/064335
§ 371 (c)(1),
(2) Date: Nov. 21, 2014

(87) PCT Pub. No.: WO2013/176214
PCT Pub. Date: Nov. 28, 2013

(65) Prior Publication Data
US 2015/0108364 A1 Apr. 23, 2015

(30) Foreign Application Priority Data

May 24, 2012 (JP) ................................. 2012-118424
May 24, 2012 (JP) ................................. 2012-118435
May 24, 2012 (JP) ................................. 2012-118437

(51) Int. Cl.
*H01J 49/10* (2006.01)
*H01J 33/00* (2006.01)
*H01J 37/18* (2006.01)
(Continued)

(52) U.S. Cl.
CPC ... *F24F 3/16* (2013.01); *A61L 9/22* (2013.01); *F04D 17/08* (2013.01); *F04D 29/422* (2013.01); *F04D 29/424* (2013.01); *F04D 29/464* (2013.01); *F04D 29/701* (2013.01); *F21V 33/0096* (2013.01); *F24F 3/166* (2013.01);
(Continued)

(58) Field of Classification Search
CPC . H01J 2237/0458; H01J 37/265; H01J 37/18; H01J 37/301; F16J 15/006
USPC ................. 250/441.11, 430, 435, 438, 492.3, 250/423 R, 306, 310; 422/121
See application file for complete search history.

(56) References Cited

U.S. PATENT DOCUMENTS

| 4,584,479 A * | 4/1986 | Lamattina et al. ........ 250/441.11 |
| 8,560,249 B2 * | 10/2013 | Nagano et al. .................. 702/24 |

(Continued)

FOREIGN PATENT DOCUMENTS

| JP | 02-184312 A | 7/1990 |
| JP | 2002-345944 A | 12/2002 |

(Continued)

*Primary Examiner* — Nikita Wells
(74) *Attorney, Agent, or Firm* — Keating & Bennett, LLP

(57) ABSTRACT

A charged particle emission and air-blowing device includes a communication port biased toward an end portion in a predetermined direction with respect to an air outlet, and a width expander configured to widen a flow path between an air directing plate of the end portion and a second blowing duct wider than a periphery. Emitted light from a light guide plate is reflected by the air directing plate in the delivery direction of an air flow. An air flow passes from a downward direction to an upward direction along a circuit board in an auxiliary suction path, and an opening portion faces the upper portion of the circuit board.

6 Claims, 13 Drawing Sheets

(51) Int. Cl.
| | |
|---|---|
| *A61J 9/00* | (2006.01) |
| *F24F 3/16* | (2006.01) |
| *F24F 13/062* | (2006.01) |
| *A61L 9/22* | (2006.01) |
| *F04D 17/08* | (2006.01) |
| *F04D 29/42* | (2006.01) |
| *F04D 29/46* | (2006.01) |
| *F04D 29/70* | (2006.01) |
| *F21V 33/00* | (2006.01) |
| *F24F 13/20* | (2006.01) |

(52) U.S. Cl.
CPC ....... *F24F 13/062* (2013.01); *F24F 2003/1682* (2013.01); *F24F 2013/205* (2013.01)

(56) References Cited

U.S. PATENT DOCUMENTS 8,691,158 B2 * 4/2014 Hanai et al. ............ 422/306
2012/0014840 A1   1/2012 Hanai et al.

FOREIGN PATENT DOCUMENTS

| | | |
|---|---|---|
| JP | 2008-025912 A | 2/2008 |
| JP | 2010-080425 A | 4/2010 |
| JP | 2010-287321 A | 12/2010 |
| JP | 2011-228075 A | 11/2011 |

* cited by examiner

CHARGED PARTICLE EMISSION DEVICE AND AIR-BLOWING DEVICE

BACKGROUND OF THE INVENTION

1. Field of the Invention

The present invention relates to a charged particle emission device and an air-blowing device.

2. Description of the Related Art

A charged particle emission device of the related art is disclosed in Japanese Unexamined Patent Application Publication No. 2010-287321 (see, for example, pages 4 to 10 and FIG. 1). The charged particle emission device includes a housing having an air outlet and a suction port in the upper surface and a side surface, respectively. A duct that communicates between the suction port and the air outlet is provided in the housing, and a blower fan is arranged in the duct. An air directing plate that guides an air flow passing through the duct in a predetermined direction is arranged in the air outlet. An ion generating element that releases ions, which are charged particles, to the exhaust side of the blower fan, is arranged in the housing.

The air flow introduced into the duct from the suction port by driving of the blower fan includes ions generated by the ion generating element. The air flow including ions is delivered from the air outlet towards the head portion of a user through guidance by the air directing plate. Therefore, it is possible to perform disinfection, deodorizing or the like in the vicinity of the user through the ion along with obtaining a pleasant cooling sensation for the user due to the blowing air.

Various air-blowing devices have been proposed as tabletop air-blowing devices. Ordinarily, the air-blowing device includes a housing having a suction port and an air outlet, and air sucked in from the suction port is blown from the air outlet by flowing through the inside of the housing.

Incidentally, the humidifying device of Japanese Unexamined Patent Application Publication No. 2008-025912 includes a main body with a blowing device and a unit for humidifying in the air flow path formed to communicate the suction port with the air outlet, a transparent or semi-transparent outlet frame provided in the air outlet, and a unit for emitting light that emits light toward the outlet frame. It is possible to notify the user that the device is operating by the unit for generating light and illuminating the outlet frame, and of the outlet direction of the air flow.

The air-blowing device in Japanese Unexamined Patent Application Publication No. 2010-80425 (see, for example, pages 6 to 14 and FIG. 1) includes a housing having an air outlet in the upper surface and suction ports in both opposing side surfaces. Filters are arranged facing each other in each suction port. A blower fan formed from a centrifugal fan in which the axial direction is horizontally arranged is arranged in the housing.

The blower fan is formed in a double-face suction type in which intake ports are opened at both surfaces in the axial direction of the casing. Each intake port of the blower fan is arranged facing the suction port in both side surfaces of the housing. The exhaust port of the blower fan is arranged facing upward. A blowing duct that communicates between the exhaust port and the air outlet is provided in the housing. A circuit board is arranged between the blowing duct and the inner wall of the housing.

The air flow sucked into the housing from both suction ports by driving of the blower fan passes to the blower fan via the intake port. The air flow passing through the blower fan and flowing out of the exhaust port ascends the blowing duct and is delivered from the air outlet.

As a first problem, according to the charged particle emission device of Japanese Unexamined Patent Application Publication No. 2010-287321, air is blown in a focused manner toward the user because the air directing plate is fixed. Therefore, ions are insufficiently diffused in the room, and sufficient disinfection effects or deodorizing effects due to the ions are not obtained. On the other hand, although it is possible to deliver ions toward the periphery when the air directing plate is formed to be movable, a pleasant cooling sensation may not be obtained because the air is not blown toward the user in a focused manner. Accordingly, a problem arises of poor convenience in the charged particle emission device.

As a second problem, the light emitting unit (outlet frame or unit for emitting light) of the humidifying device in Japanese Unexamined Patent Application Publication No. 2008-025912 is exposed, and a problem of the device being glaring arises because of the user directly viewing the light emitting unit.

As a third problem, according to the air-blowing device in Japanese Unexamined Patent Application Publication No. 2010-80425, it becomes necessary to provide a large heat dissipation space for the circuit board in the housing in order to prevent breakdown of electrical components in the housing due to heat generated by the circuit board. In so doing, a problem arises of the air-blowing device increasing in size.

SUMMARY OF THE INVENTION

Preferred embodiments of the present invention provide a charged particle emission device which is able to improve a convenience of use. Another advantage of some preferred embodiments of the present invention is to provide an air-blowing device that reduces the amount of light emitted in the blowing direction during use, and in which it is difficult to directly view the light emitting unit. Still another advantage of some preferred embodiments of the present invention is to provide an air-blowing device which is able to achieve a reduction in size.

According to a preferred embodiment of the present invention, a charged particle emission device includes a housing with a suction port and an air outlet; a blower fan in the housing; a first blowing duct on the exhaust side of the blower fan; a second blowing duct in which an air outlet is opened at one end and configured to communicate with the first blowing duct via a communication port; a charged particle generating element configured to release charged particles in the first blowing duct; a wind direction plate configured to radially guide an air flow and located opposite to the air outlet; and a width expander configured such that the communication port is biased with respect to the one end in a predetermined direction with respect to the air outlet, and configured such that the width expander widens a flow path between the second blowing duct and the air directing plate on the one end wider than a periphery.

According to the above-described configuration, when the blower fan is driven, air flow sucked into the housing from the suction port passes through the first blowing duct by passing through the blower fan. Charged particles generated by the charged particle generating element are included in the air flow that passes through the first blowing duct. The air flow including the charged particles passes to the second blowing duct via the communication port, and is guided to the air outlet by passing through the second blowing duct. The air flow that passes from the air outlet is delivered radially from between the air directing plate and the housing by guidance of the air directing plate. In so doing, the charged particles are diffused in the room. The communication port is eccentric with respect to the air outlet, for example, forward, and a flow path of the front portion between the air directing plate and the second blowing duct widens farther than the periphery due to the width expander. In so doing, the flow rate of the air flow delivered forward from between the air directing plate and the housing is increased, and the air flow is delivered in a focused manner toward a user.

In the charged particle emission device, it is preferable that the width expander include a concave portion provided in an inner wall of the second blowing duct.

In the charged particle emission device, it is preferable that flow path area widens as the second blowing duct progresses toward the air outlet, and a cross-sectional shape of an inner surface of the concave portion perpendicular or substantially perpendicular to the air outlet define an inclined straight line and the cross-sectional shape of the inner surface of around the concave portion perpendicular or substantially perpendicular to the air outlet define a convex curve which is inclined relative to an inside.

According to the above-described configuration, the inner wall of the second blowing duct preferably has, for example, a horn shape in which a cross-sectional shape at a periphery of the concave portion is a curve, and preferably defines a conical plane where the cross-sectional shape at the concave portion is a straight line.

In the charged particle emission device, it is preferable that the width expander includes a notch portion extending in a predetermined direction in the air directing plate. According to the above-described configuration, for example, planar shapes of the air outlet and the air directing plate preferably are circular or substantially circular with the same or substantially the same diameter, and the notch portion in which a portion with respect to the circular or substantially circular shape is notched is defined in a portion of the air directing plate.

The charged particle emission device may further include an air direction varying portion provided at the communication port and configured to guide the air flow passing through the first blowing duct in a predetermined direction. According to the above-described configuration, the communication port is eccentric with respect to the air outlet, for example, forward, and the air flow passing through the first blowing duct is guided forward by the air direction varying portion provided at the communication port.

In the charged particle emission device, it is preferable that the charged particles include both positive ions and negative ions, for example. According to the above-described configuration, a disinfectant effect and a deodorizing effect are obtained due to the positive ions and negative ions diffused in the room, and a moisturizing effect for the skin of the user is obtained due to the positive ions and negative ions delivered toward the user.

According to another aspect of various preferred embodiments of the present invention, an air-blowing device includes a housing including a suction port and an air outlet; a blower fan in the housing; a light source in the housing; a light guide plate including a communication port, guiding incident light from an incident surface facing the light source, and emitting the light from an emission surface facing the air outlet; a first duct communicating between the blower fan and the communication port; a second duct communicating between the air outlet and the communication port; and an air directing plate radially delivering an air flow and facing the air outlet; wherein the communication port is biased with respect to the air outlet and the emitted light from the light guide plate is reflected in a delivery direction of the air flow by the air directing plate.

According to the above-described configuration, since the communication port in the light guide plate is biased with respect to the air outlet, the light emitting area of the light guide plate in the region in which the communication port is defined is small as compared to the light emitting area of the light guide plate in other regions. In other words, since the light emission amount with respect to the air blowing direction is reduced, an amount of glare is significantly reduced. In addition, light emitted from the light guide plate is reflected in the delivery direction of the air flow by the air directing plate. In other words, the light emitted from the light guide plate is reflected by the air directing plate, thus performing indirect illumination of the periphery of the air-blowing device. Accordingly, the amount of glare is significantly reduced since it is not easily directly viewed by the user.

In the air-blowing device, it is preferable that the light guide plate include an air direction varying portion configured to direct the air flow passing through the communication port in a predetermined direction.

According to the above-described configuration, since the air direction varying portion preferably is defined in the light guide plate, it is not necessary to provide the air direction varying portion as a separate component. Accordingly, the size of the overall air-blowing device does not increase.

In a preferred embodiment of the air-blowing device, it is preferable that the air directing plate include a shaft portion extending through the light guide plate and supported by the housing, and that the communication port be located on an opposite side of an incident surface with respect to the shaft portion.

According to the above-described configuration, a shaft portion is interposed between the incident surface and the communication port. In other words, a portion of the light emitted from the light source and guided by being incident from the incident surface is blocked by the shaft portion. Accordingly, luminance of the light guide plate in a region in which the communication port is located becomes lower as compared to luminance of the light guide plate in other regions. Accordingly, the amount of glare is significantly reduced.

In the air-blowing device, it is preferable that the air directing plate is configured to move between a position that covers the air outlet and a position that opens the air outlet, and the light source is lit when the air outlet is opened.

According to the above-described configuration, since the light source is lit if the air-blowing device is in an operating state, and the light source is turned off if in a stopped state, it is possible to easily determine a working state.

According to still another preferred embodiment of the present invention, an air-blowing device includes a housing including a suction port and an air outlet; a blower fan including a centrifugal fan covered by a casing and arranged horizontally or substantially horizontally in an axial direction, and in which a first intake port facing the suction port is opened at one surface in the axial direction of the casing and a second intake port is opened at another surface; a circuit board vertically extending in the housing; a dividing wall including an opening portion that faces the second intake port and isolating the blower fan and the circuit board; a suction duct communicating between the suction port and the first intake port; and an auxiliary suction path guiding air flow from the suction port to the second intake port via the opening portion; wherein the air flow passes from below to above along the circuit board in the auxiliary suction path, and the opening portion faces an upper portion of the circuit board.

According to the above-described configuration, the air flow sucked into the suction duct from the suction ports when the blower fan is driven passes into the casing of the blower fan via the first intake port. A portion of the air flow passes through the auxiliary suction path, and the circuit board is cooled by the air flow ascending along the circuit board side of the dividing wall along the circuit board. The air flow ascending along the circuit board is guided to the blower fan side of the dividing wall via the opening portion facing the upper portion of the circuit board and passes to the casing of the blower fan via the second intake port. The air flow passing out of the blower fan is delivered from the air outlet.

In the above-described air-blowing device, it is preferable that a step portion be provided on the dividing wall such that a gap between the second intake port and an upper portion thereof is wider than a gap between the second intake port and a lower portion thereof, and the opening portion with a smaller area than the second intake port be provided at the upper portion on the dividing wall. According to the above-described configuration, the dividing wall approaches the air blowing fan, and, thus, the air flow passing in the auxiliary suction path ascends along the circuit board from the lower portion separated from the circuit board. The air flow is guided to the second intake port of the blower fan via the opening portion on the step portion by which the diving wall and the blower fan are separated.

The air-blowing device may further include a box-shaped duct member defining the suction duct facing the suction port, wherein the dividing wall is defined by a wall surface facing the suction port, and the auxiliary suction path is defined between a chamfered outer surface provided on a lower end of one side of wall adjacent to the dividing wall and the housing.

According to the above-described configuration, the opening surface of the box-shaped duct member faces the suction port, and air flow suctioned in from the suction port is guided to the first intake port of the blower fan by passing through the suction duct formed by the duct member. A portion of the air flow sucked in from the suction port passes in a direction parallel or substantially parallel to the suction duct between the chamfer provided on the bottom surface of the one side wall of the duct member and the housing.

The air-blowing device may further include a blowing duct communicating between the blower fan and the air outlet; and a pair of discharge electrodes configured to release positive charged particles and negative charged particles into the blowing duct, in which the discharge electrodes are parallel or substantially parallel in the axial direction of the blower fan. According to the above-described configuration, positive charged particles and negative charged particles released from the discharge electrodes are included in the air flow that passes through the blowing duct, and are delivered from the air outlet.

According to a preferred embodiment of the present invention, the communication port of the first and second blowing ducts is biased to one end portion with respect to the air outlet, and the width expander is provided to widen the end portion of the flow path between the air directing plate that guides the air flow radially by facing the air outlet and the second blowing duct wider than the periphery. In so doing, it is possible for charged particles to be diffused in the room by delivering the air flow including charged particles from the periphery along with being able to perform air blowing in a focused manner toward the user. Accordingly, it is possible to improve the convenience of the charged particle emission device.

Since the communication port is preferably defined in the light guide plate biased with respect to the air outlet, the light emitting area of the light guide plate in the region in which the communication port is defined is small as compared to the light emitting area of the light guide plate in other regions. In other words, since the light emission amount with respect to the air blowing direction is significantly reduced, the amount of glare is significantly reduced. In addition, light emitted from the light guide plate is reflected in the delivery direction of the air flow by the air directing plate. In other words, the light emitted from the light guide plate is reflected by the air directing plate, thus performing indirect illumination of the periphery of the air-blowing device. Accordingly, an amount of glare is significantly reduced since it is not easily directly viewed by the user.

A suction duct that is configured to guide the air flow from the suction port to the first intake port and an auxiliary suction path that is configured to guide the air flow to the second intake port via the opening portion facing the upper portion of the circuit board are preferably provided, and the air flow passes from a downward direction to an upward direction along the circuit board in the auxiliary suction path. In so doing, cooling is possible from the lower portion to the upper portion of the circuit board by the air flow that ascends toward the opening portion. Accordingly, it is possible to achieve size reductions in the air-blowing device by reducing the heat dissipation space in the housing of the circuit board.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

First Preferred Embodiment

Figure 1:
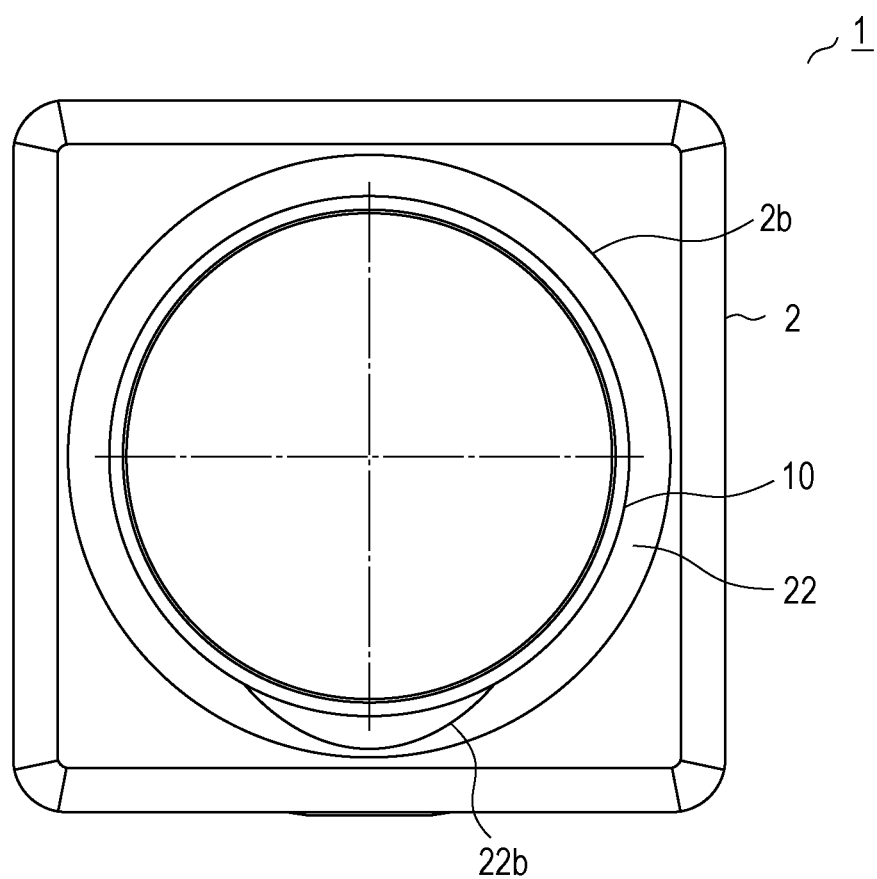
FIG. 1 is a top view illustrating a charged particle emission device of a first preferred embodiment of the present invention.
Figure 2:
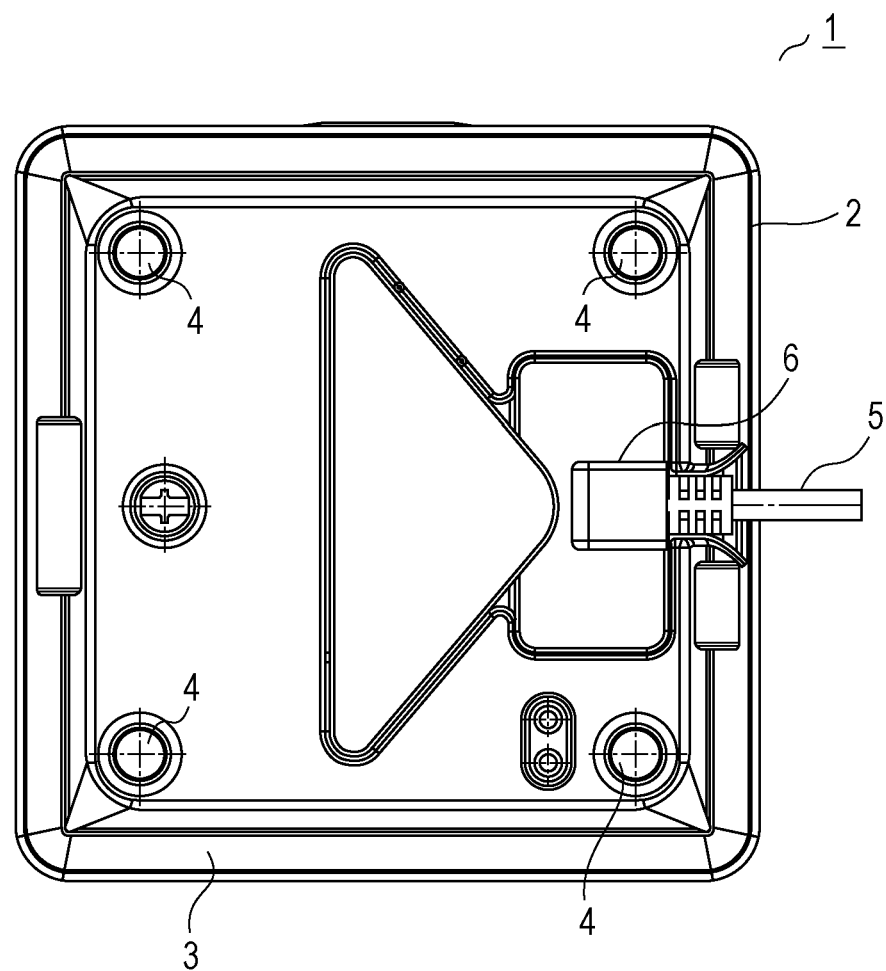
FIG. 2 is a bottom view illustrating the charged particle emission device of the first preferred embodiment of the present invention.
Figure 3:
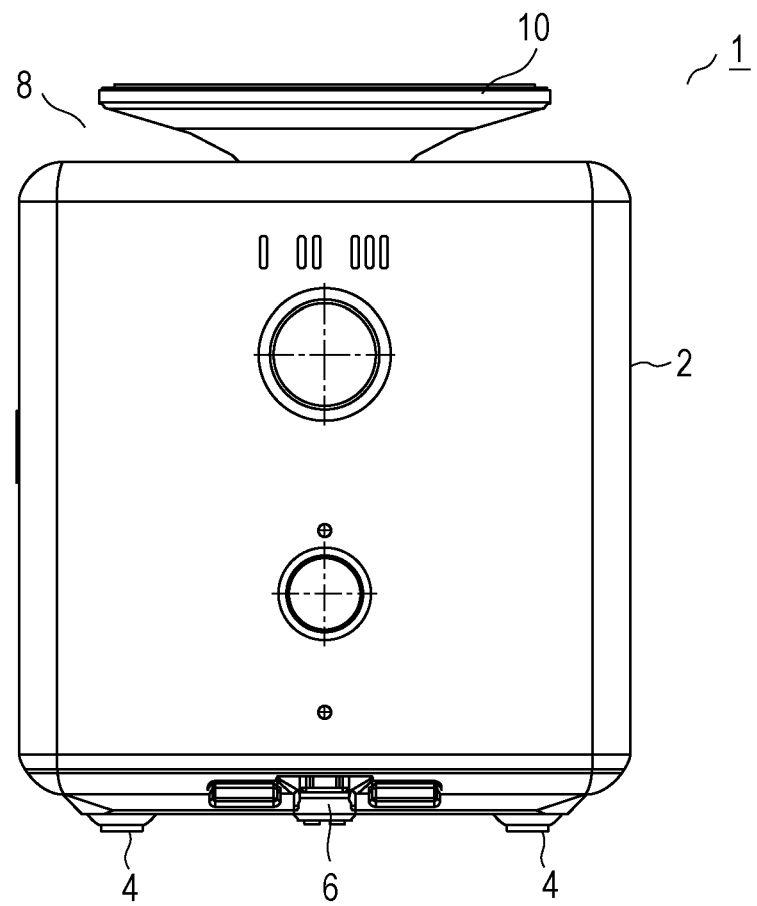
FIG. 3 is a left side view illustrating the charged particle emission device of the first preferred embodiment of the present invention.
Figure 4:
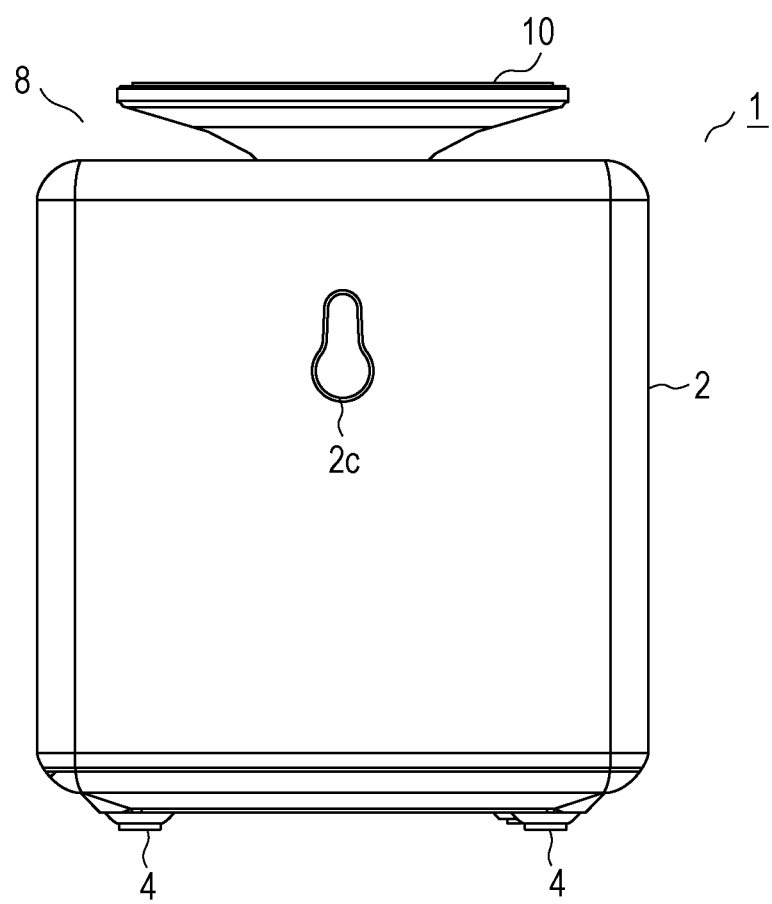
FIG. 4 is a rear view illustrating the charged particle emission device of the first preferred embodiment of the present invention.

Below, preferred embodiments of the present invention will be described with reference to the drawings. FIGS. 1 to 4 are, respectively, a top view, bottom view, left side view, and rear view of the charged particle emission device of the first preferred embodiment. The charged particle emission device 1 preferably includes a cube-shaped housing 2, and an air outlet 2b is opened at the upper surface by opening a suction port 2a (refer to FIG. 6) in the left side surface of the housing 2. The air outlet 2b preferably is circular or substantially circular, and an air directing plate 10 that is supported to be vertically movable with respect to the housing 2 is located opposite to the air outlet 2b.

Although description below is made by applying the reference numeral 1 to the charged particle emission device that is a type of air-blowing device, the charged particle emission device 1 may be read interchangeably as the air-blowing device 1.

The bottom plate 3 of the housing 2 is provided to be attachable and detachable, and rubber legs 4 are preferably provided at the four corners of the bottom plate 3. In so doing, it is possible to use the charged particle emission device 1 while located on a table top or the like. A latching hole 2c in which a hook provided on a wall surface in the room is latched is provided in the rear surface of the housing 2. In so doing, it is possible to use the charged particle emission device 1 latched to a wall surface.

A power cord 5 is preferably connected to the right end portion of the bottom surface of the housing 2. The power cord 5 is connected to a plug 6 provided at one end by being inserted in a power terminal 35 (refer to FIG. 6) via an insertion hole 3a (refer to FIG. 6) provided in the bottom plate 3. Power is supplied to the charged particle emission device 1 by connecting the other end of the power cord 5 to a power supply source, such as, for example, a commercial power supply, a USB terminal, etc.

Figure 5:
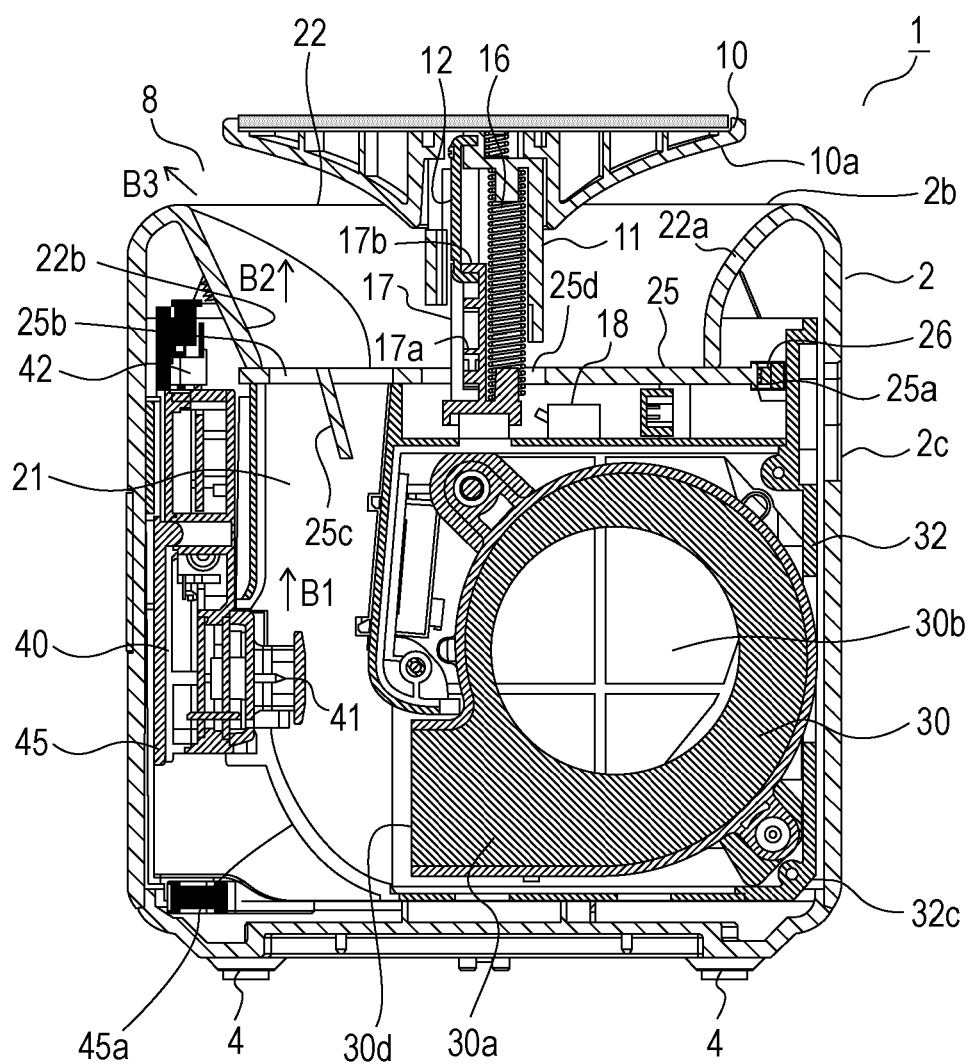
FIG. 5 is a right side cross-sectional view illustrating the charged particle emission device of the first preferred embodiment of the present invention.
Figure 6:
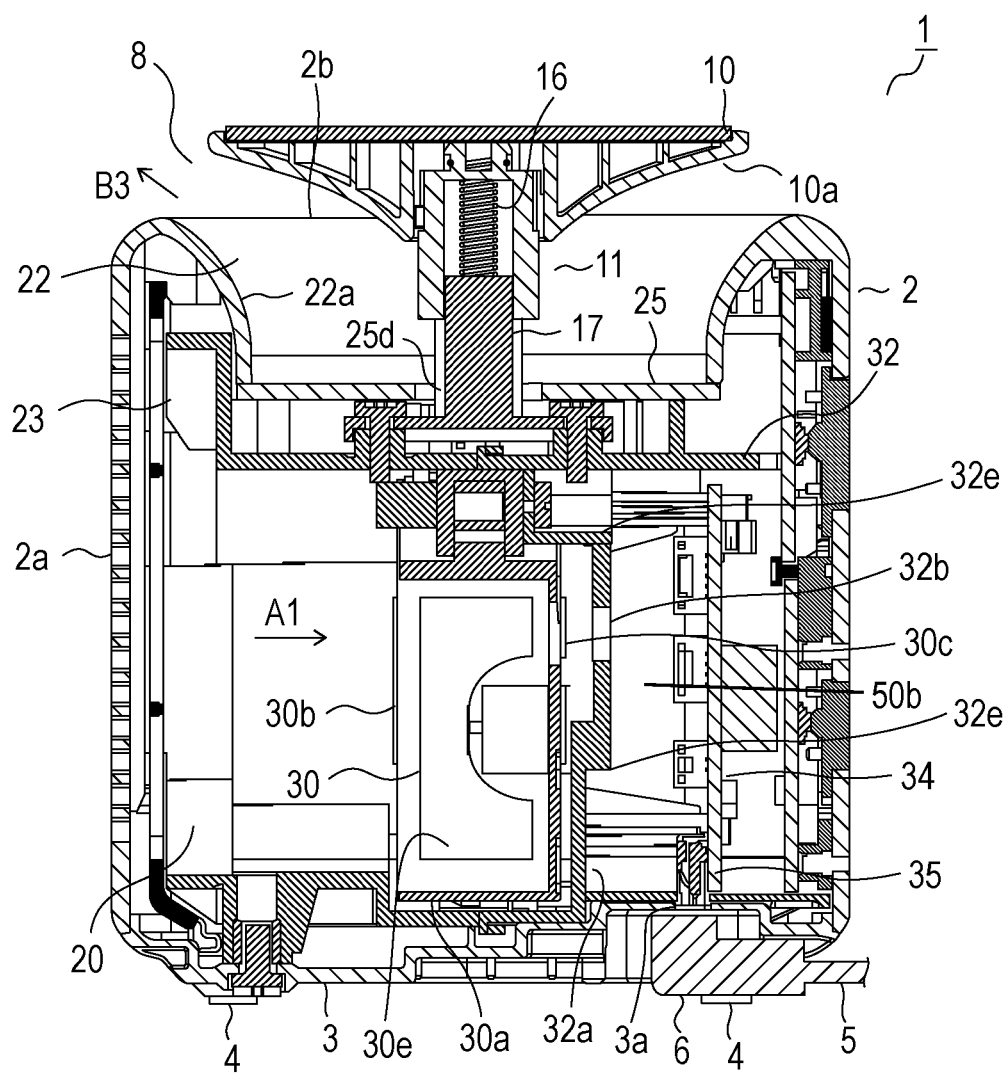
FIG. 6 is a front cross-sectional view illustrating the charged particle emission device of the first preferred embodiment of the present invention.

FIGS. 5 and 6 are, respectively, a right side cross-sectional view and a front surface cross-sectional view of the charged particle emission device 1. The air directing plate 10 preferably has a circular or substantially circular planar shape with the same or substantially the same diameter as the air outlet 2b, and the lower surface 10a is defined in a circular truncated cone or substantially circular truncated cone shape defined by an inclined surface, for example. A sleeve 11 is preferably attached to the center portion of the air directing plate 10. The sleeve 11 fits with the shaft portion 17 located in the housing 2, vertically movable with respect to the housing 2 integral with the air directing plate 10. The shaft portion 17 passes through the through hole 25d opened at the center of the light guide plate 25, described later, and is supported by the duct member 32 located in the housing 2.

A compression spring 16 that vertically biases the air directing plate 10, and first and second engaging claws 17a and 17b are preferably located on the shaft portion 17 in the vertical direction. An engaging member 12 that engages with the first and second engaging claws 17a and 17b is attached inside the sleeve 11. A power switch 18 is located in the upper surface of the duct member 32.

The air directing plate 10 biased by the compression spring 16 moves between a position that opens the air outlet 2b and a position that closes the air outlet 2b by engagement of the first and second engaging claws 17a and 17b and the engaging member 12. That is, when the engaging member 12 engages the upper second engaging claw 17b as shown in the same drawing, the air outlet 2b is opened. At this time, the power switch 18 is in the on state.

Figure 7:
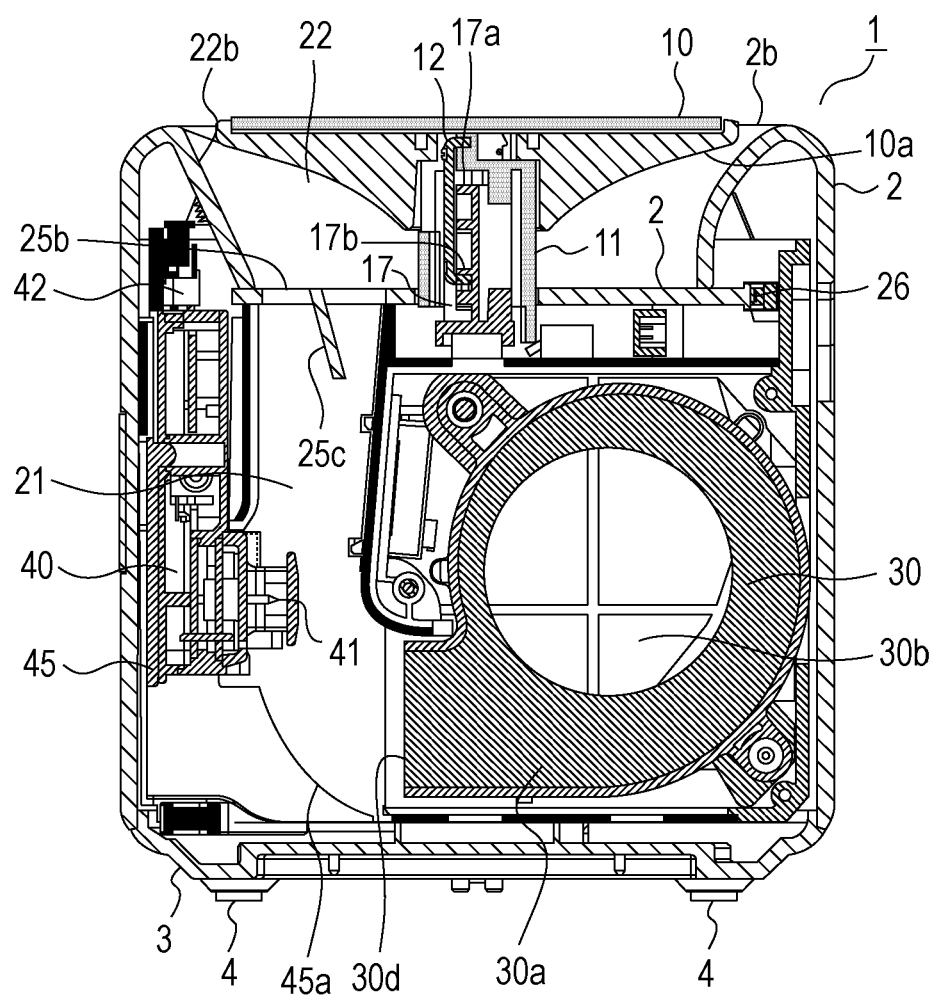
FIG. 7 is a right side cross-sectional view illustrating a state in which the air outlet of the charged particle emission device of the first preferred embodiment of the present invention is closed.

When the engaging member 12 engages the lower first engaging claw 17a as shown in FIG. 7 by pushing the air directing plate 10 down from the open state of the air outlet 2b, the air outlet 2b is closed by the air directing plate 10. At this time, the power switch 18 enters the off state by the sleeve 11 coming in contact with the power switch 18. When the air directing plate 10 is pushed down from the state in which the air outlet 2b is closed, the air directing plate 10 pops up as shown in FIG. 5.

In so doing, the power switch 18 is turned on and off by the vertical motion of the air directing plate 10, and the blower fan 30, the ion generating element 40 and the LED 26, described later, are driven with the power switch 18 in the on state. When the air outlet 2b is opened, an annular outflow portion 8 from which the air flow is radially delivered from between the air outlet 2b and the air directing plate 10 by the air directing plate 10 with the same or substantially the same diameter as the air outlet 2b is defined.

The duct member 32 is preferably located in the lower portion of the housing 2, and is defined in a box shape in which one end of the opening surface faces the suction port 2a. A blower fan 30 provided by a centrifugal fan, such as, for example, a sirocco fan, covered by a casing 30a is located in the duct member 32. The blower fan 30 is arranged horizontally in the axial direction and held by being screwed to a fan holding portion 32a defined in the right side wall of the duct member 32.

Intake ports 30b and 30c (first and second intake ports) are opened at both sides in the axial direction in the casing 30a, and an exhaust port 30d is opened at the end surface in the circumferential direction. A suction duct 20 is configured to communicate between the suction port 2a with one intake port 30b by the duct member 32. A filter 23 that is removable from the bottom surface of the housing 2 is preferably located in the suction port 2a.

Figure 8:
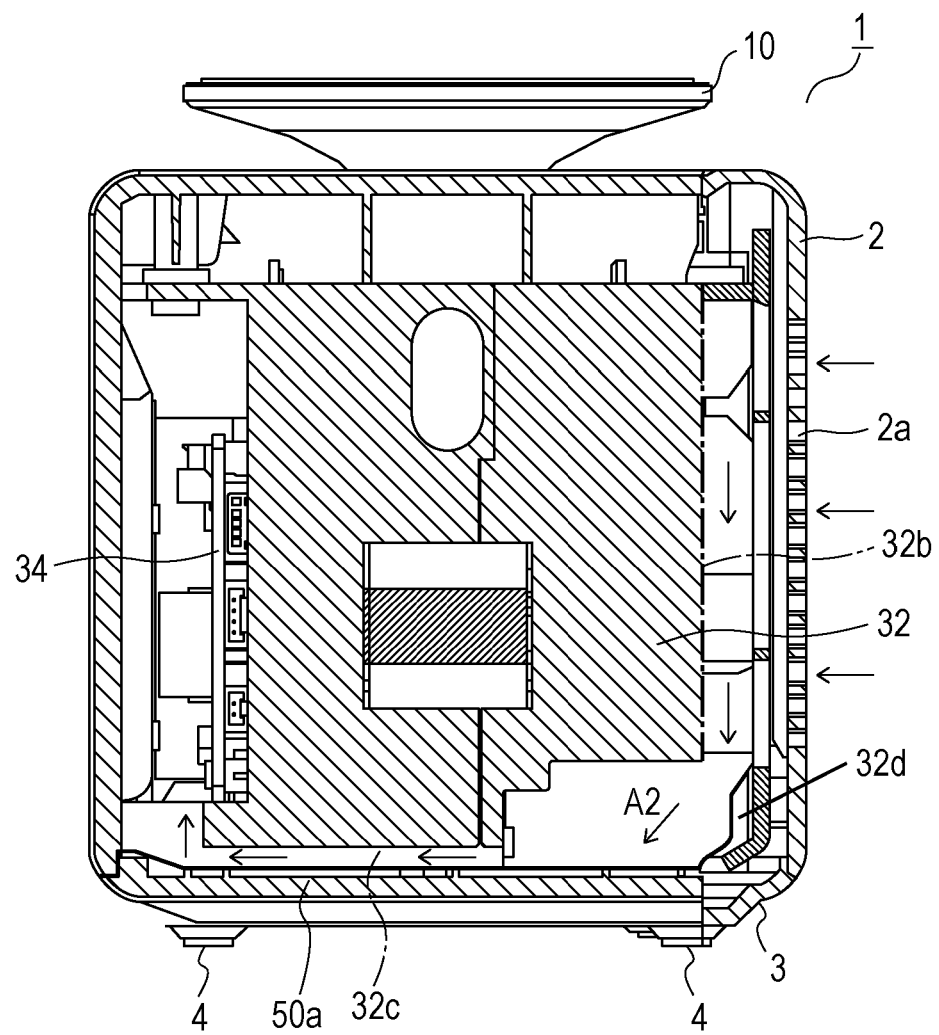
FIG. 8 is a rear cross-sectional view illustrating the charged particle emission device of the first preferred embodiment of the present invention.

A step portion 32e is separated from the intake port 30c with respect to the bottom portion in the upper portion of the right side wall of the duct member 32. An opening portion 32b with a smaller opening area than the intake port 30c is opened with respect to the intake port 30c in the step portion 32e. The notch portion 32d (refer to FIG. 8) is provided in the right end portion facing the suction port 2a on the rear surface side of the duct member 32. The chamfer 32c is defined in the bottom portion of the rear surface side of the duct member 32, and a channel 50a is parallel or substantially parallel to the suction duct 20 between the chamfer 32c and the inner surface of the housing 2.

The circuit board 34 on which electronic components, such as the power terminal 35, are mounted is preferably arranged upright to the right of the duct member 32. In so doing, a dividing wall that isolates the blower fan 30 and the circuit board 34 is preferably defined by the fan holding portion 32a, and the channel 50b is defined between the outer surface of the dividing wall and the inner surface of the housing 2.

The air flow passing from the suction port 2a to the suction duct 20 by the driving of the blower fan 30 is guided to the intake port 32b as shown in by the arrow A1. As shown in by the arrow A2 in the rear surface cross-sectional view in FIG. 8, a portion of the air flow passes downward by flowing out from the duct member 32 via the notch portion 32d, and passes to the left in the outside of the chamfer 32c. The air flow passes upward between the circuit board 34 and the duct holding portion 32a, and is guided to the intake port 32c via the opening portion 32b.

Accordingly, the channels 50a and 50b branch from the suction duct 20, thus defining the auxiliary suction path that guides the air flow from the suction port 2a to the intake port 30c. In so doing, the air flow is sucked in from both surfaces in the axial direction of the blower fan 30 via a plurality of channels, and it is possible to improve the blowing efficiency. It is possible to stop biasing in the flow rate in the axial direction, and deliver a uniform air flow from the blower fan 30. The auxiliary suction path approaching the suction port 2a may be provided without providing the notch portion 32d.

It is possible to cool the electronic components mounted to the circuit board 34 with the air flow passing through the channel 50b. At this time, the opening portion 32b is provided below with respect to the center of the blower fan 30 and on the step portion 32e of the upper portion of the duct holding portion 32a, and preferably has a smaller diameter than the intake port 30c with respect to the upper portion of the uprightly arranged circuit board 34. In so doing, it is possible to reliably cool from the lower portion to the upper portion of the circuit board 34 by the air flow passing from below toward the opening portion 32b from below.

Because the duct holding portion 32a approaches the blower fan 30 beneath the step portion 32e, the flow path of the lower portion of the channel 50b which the air flow warps and passes to from the channel 50a is secured to be wide. In addition, because the intake port 30c and the duct holding portion 32a are separated by the step portion 32e, it is possible to diffuse the air flow from the small diameter opening portion 32b, and guide the air flow to the large diameter intake port 30c. Accordingly, it is possible to further improve the blowing efficiency.

The first blowing duct 21 is provided in front of the exhaust port 30d of the blower fan 30. A second blowing duct 22 in which the air outlet 2b is opened is provided above the first blowing duct 21. The first blowing duct 21 and the second blowing duct 22 communicate via the communication port 25b of the light guide plate 25, described later.

Figure 9:
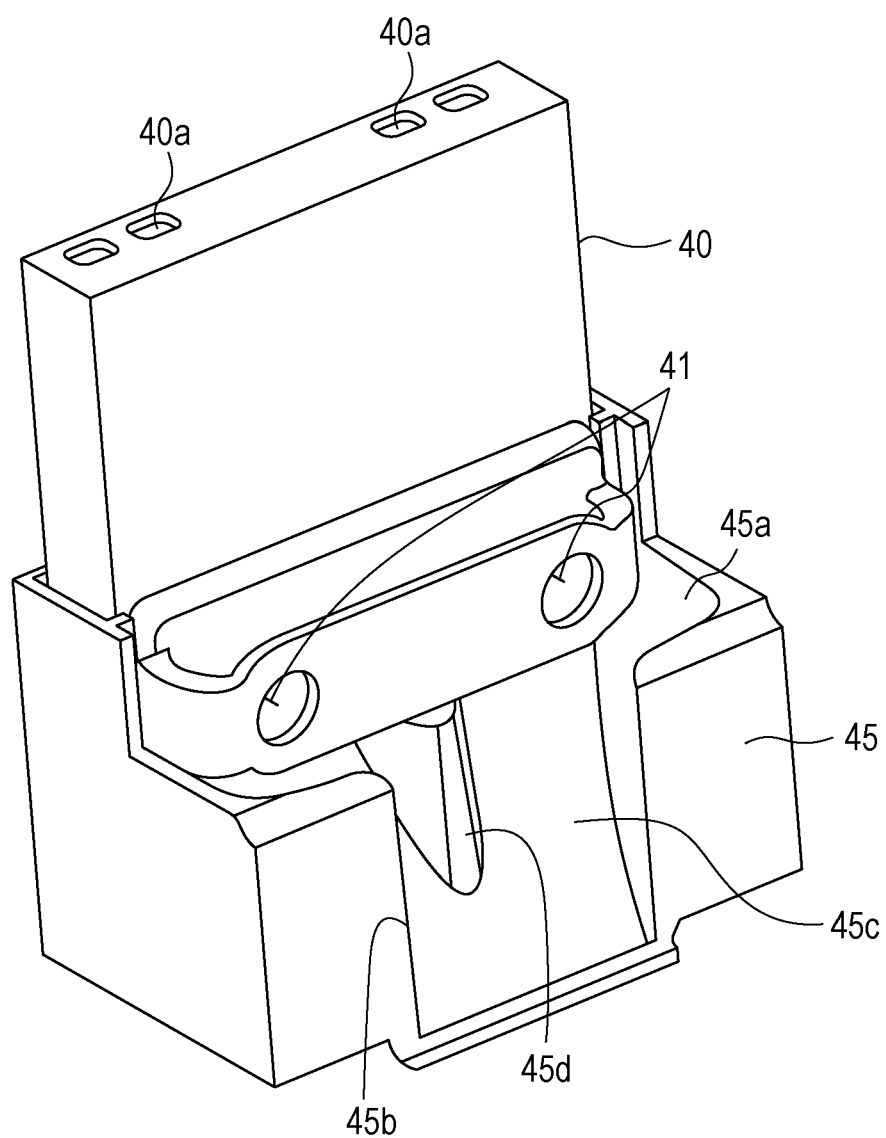
FIG. 9 is a perspective view illustrating the holding member and the ion generating element of the charged particle emission device of the first preferred embodiment of the present invention.

The upper portion of the first blowing duct 21 is preferably defined by the duct member 32, and the lower portion is defined by the holding member 45 that holds the ion generating element 40 and is adjacent to the exhaust port 30d. FIG. 9 is a perspective view of the holding member 45 holding the ion generating element 40. The holding member 45 includes a bend section 45a in which the flow path is widened in the left-to-right direction by the opening portion 45b with the same or approximately the same width in the left-to-right direction as the exhaust port 30d being opened at the rear end surface.

The front wall 45c of the bend section 45a preferably includes a curved surface continuous with the lower end of the casing 30a of the blower fan 30, and is inclined to face the exhaust port 30d. In so doing, the air flow is warped and guided upward via the bend section 45a. At this time, the air flow delivered from the exhaust port 30b impacts on the front wall 45c of the bend section 45a, and decelerates due to dynamic pressure being converted to static pressure. The dynamic pressure is also converted to static pressure due to the widening of the flow path by the bend section 45a, further decelerating the air flow. Accordingly, the bend section 45a defines a static pressure converter that is configured to convert the dynamic pressure of the air flow to static pressure.

A partition plate 45d extending vertically to the center portion facing the opening portion 45b is provided in the front wall 45c of the bend section 45a.

The ion generating element 40 preferably includes a pair of needle-shaped discharge electrodes 41 arranged parallel or substantially parallel in the left-to-right direction (axial direction of the blower fan 30) facing the first blowing duct 21. The discharge electrodes 41 are arranged directly above the bend section 45a, and the distance between both discharge electrodes 41 is defined wider than the width of the opening portion 45b.

The discharge electrodes 41 of the ion generating element 40 generate a corona discharge by applying a high voltage in an alternating current wave form or an impulse wave form. A positive voltage is applied to one of the discharge electrodes 41, and hydrogen ions are generated by ionizing water molecules in the air using the corona discharge. The hydrogen ions cluster with the water molecules in the air due to the solvation energy. In so doing, positive ions of the air ions formed from $H^+(H_2O)m$ (m is 0 or an arbitrary natural number) are released.

A negative voltage is applied to the other of the discharge electrodes 41, and oxygen ions are generated by ionizing oxygen molecules or water molecules in the air using the corona discharge. The oxygen ions cluster with the water molecules in the air due to the solvation energy. In so doing, negative ions of the air ions formed from $O_2^-(H_2O)n$ (n is an arbitrary natural number) are released.

The $H^+(H_2O)m$ and $O_2^-(H_2O)n$ aggregate on the surfaces of floating fungi or odor components in the air, thus encompassing the surfaces thereof. As shown in formulae (1) to (3) below, the floating fungi and odor components are broken down by aggregation of the [—OH] (hydroxyl group radicals) or $H_2O_2$ (hydrogen peroxide) that are active species due to the collision on the surface of microorganisms or the like. Here, m' and n' are both arbitrary natural numbers. Accordingly, by delivering positive ions and negative ions from the air outlet 2b into the room, it is possible to perform disinfection and deodorizing in the room. When positive ions and negative ions are delivered toward the head portion of a user, it is possible to obtain a moisturizing effect for the skin of the user.

$$H^+(H_2O)m + O_2^-(H_2O)n \rightarrow \cdot OH + \tfrac{1}{2}O_2 + (m+n)H_2O \qquad (1)$$

$$H^+(H_2O)m + H^+(H_2O)m' + O_2^-(H_2O)n + O_2^-(H_2O)n' \rightarrow \\ 2 \cdot OH + O_2 + (m+m'+n+n')H_2O \qquad (2)$$

$$H+(H_2O)m + H+(H_2O)m' + O_2^-(H_2O)n + O_2^-(H_2O) \\ n' \rightarrow H_2O_2 + O_2 + (m+m'+n+n')H_2O \qquad (3)$$

By arranging the pair of discharge electrodes 41 in the left-to-right direction perpendicular or substantially perpendicular to the air flow, it is possible to prevent extinction due to the collision of positive ions and negative ions, thus increasing the delivery amount of ions.

Because the discharge electrodes 41 are arranged directly above the bend section 42a, ions generated by the discharge electrodes 41 are included in the air flow decelerated by conversion to static pressure due to the bend section 42a. In so doing, it is possible to reliably transport ions generated by the discharge electrodes 41 with the air flow, and it is possible to increase the delivery amount of ions.

At this time, because the distance between both discharge electrodes 41 is greater than the width of the opening portion 45b, and the discharge electrodes 41 are preferably located at both sides of the opening portion 45b, it is possible for the ions to be more reliably included in the decelerated air flow.

Because the blower fan 30 has the intake ports 30b and 30c in both surfaces, thus uniformly delivering the air flow in the axial direction, it is possible for the flow rate of the air flow passing in the periphery of each discharge electrode 41 to be the same or substantially the same rate. In addition, it is possible for the flow rate of the air flow passing in the periphery of each discharge electrode 41 to be the same or substantially the same rate due to the partition plate 45d, and possible for positive ions and negative ions to be uniformly included.

Figure 10:
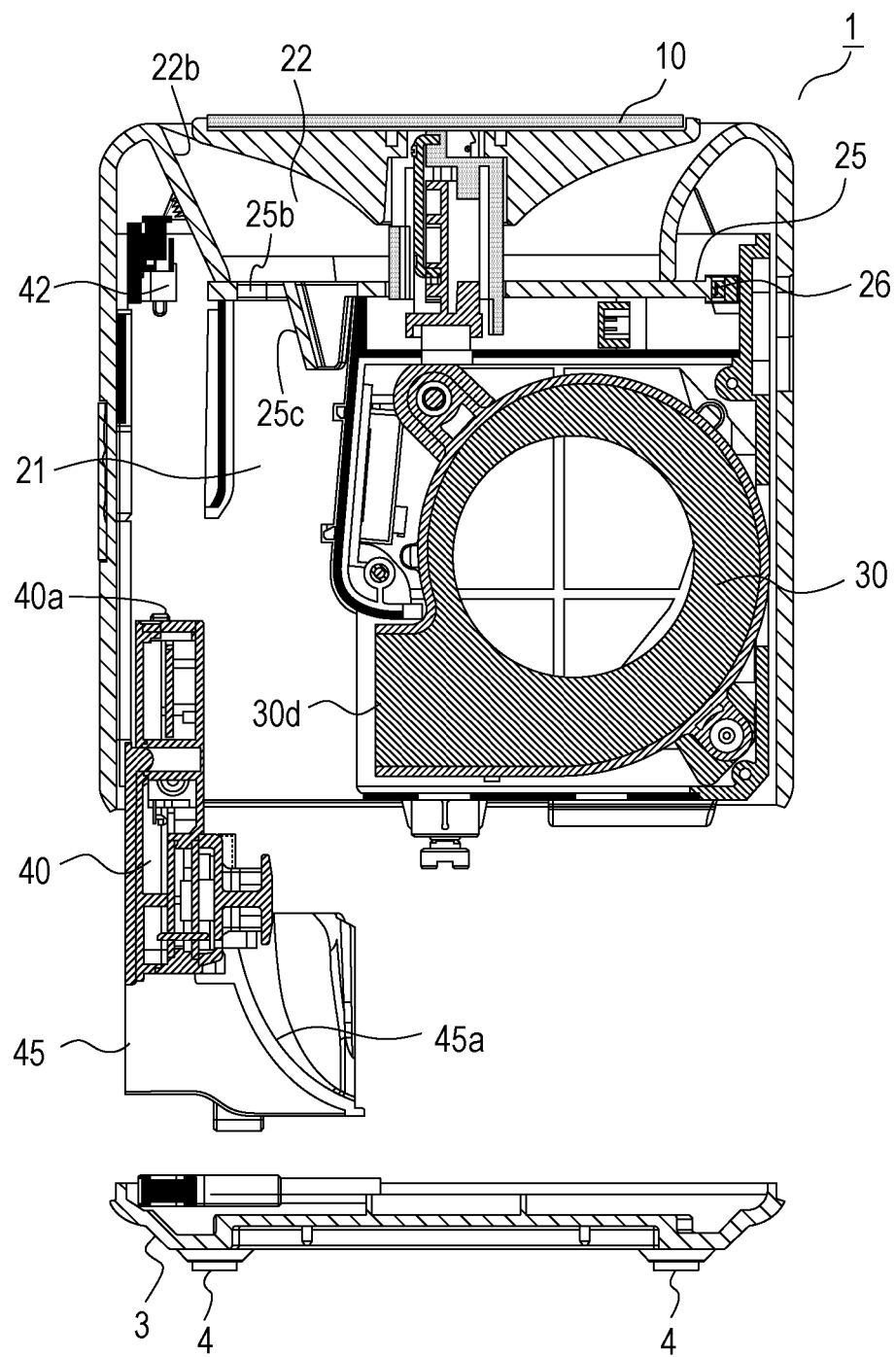
FIG. 10 is a right side cross-sectional view illustrating a state in which the bottom plate of the charged particle emission device of the first preferred embodiment of the present invention is removed.

The holding member 45 is configured to be attached and detached from the bottom surface of the housing 2 by removing the bottom plate 3, as shown in FIG. 10. In so doing, it is possible to easily exchange ion generating elements 40. In addition, it is possible to clean the blades 30e of the blower fan 30 (refer to FIG. 6) via the exhaust port 30d exposed by the removal of the holding member 45. It is possible to also attach and remove the filter 23 (refer to FIG. 6) from the bottom surface of the housing 2 by similarly removing the bottom plate 3, and possible to easily perform cleaning of the filter 23.

The ion generating element 40 includes a connection terminal 40a on the upper surface thereof. When the ion generating element 40 is mounted from below along with the holding member 45, the connection terminal 40a comes into contact with the power terminal 42 (refer to FIG. 5) provided in the housing 2, and it is thus possible to supply power to the ion generating element 40. Therefore, the weight of the ion generating element 40 is not borne by the power terminal 42, and it is possible to prevent breakdowns of the power terminal 42 due to the continuous bearing of the weight.

Figure 11:
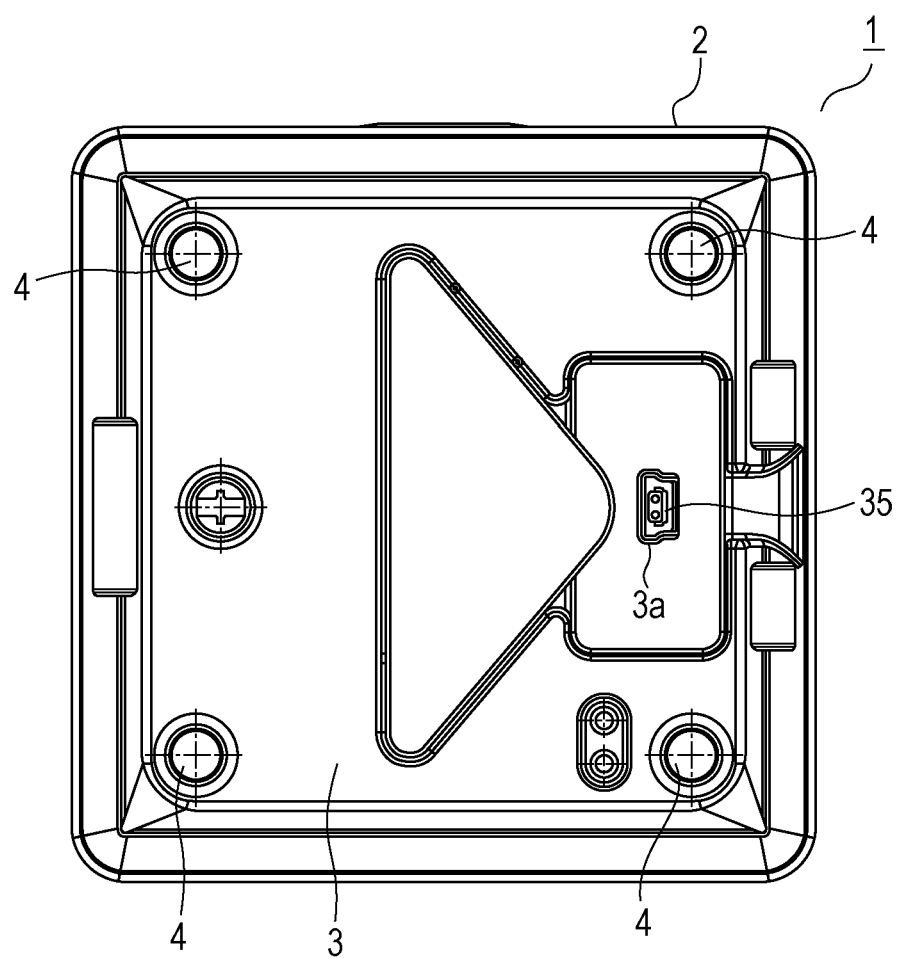
FIG. 11 is a bottom view illustrating a state in which the power cord of the charged particle emission device of the first preferred embodiment of the present invention is removed.

It is possible to remove the bottom plate 3 of the housing 2 in the state in which the plug 6 (refer to FIG. 6) of the power cord 5 is removed as shown in the bottom view of FIG. 11. In so doing, it is possible to prevent electrical shock due to being energized when the bottom plate 3 is removed.

In FIGS. 5 and 6, the light guide plate 25 is preferably arranged flat and level on the upper surface of the first blowing duct 21. The light guide plate 25 is preferably defined in a flat plate shape by a transparent member, such as, for example, acrylic, and an LED 26 (light source) is arranged facing the incident surface 25a of the rear end surface. A reflection sheet (not shown) is located on the bottom surface of the light guide plate 25.

The light emitted from the LED 26 is incident on the light guide plate 25 from the incident surface 25a and is guided, and light incident at an angle of incidence smaller than the critical angle is emitted to the upper and lower surfaces. At this time, the light emitted from the lower surface of the light guide plate 25 is reflected upward by the reflection sheet. In so doing, light is emitted toward the air outlet 2b from the upper surface (emission surface) of the light guide plate 25. A plurality of prisms that reflect the guided light upward may be provided on the lower surface of the light guide plate 25.

A through hole 25d through which the shaft portion 17 passes is opened at the center portion of the light guide plate 25, and a communication port 25b is opened at the front portion of the opposite side to the incident surface 25a with respect to the through hole 25d. Because the first blowing duct 21 is located in the front portion of the housing 2, and the communication port 25b facing the first blowing duct 21 is provided in the front portion biased with respect to the air outlet 2b.

The second blowing duct 22 is preferably provided above the light guide plate 25. The second blowing duct 22 includes the air outlet 2b in the upper surface thereof, and preferably has a cylindrical or substantially cylindrical shape concentric with the air outlet 2b. The inner wall 22a of the second blowing duct 22 includes an inclined surface in which the area of the flow path widens toward the air outlet 2b.

Figure 12:
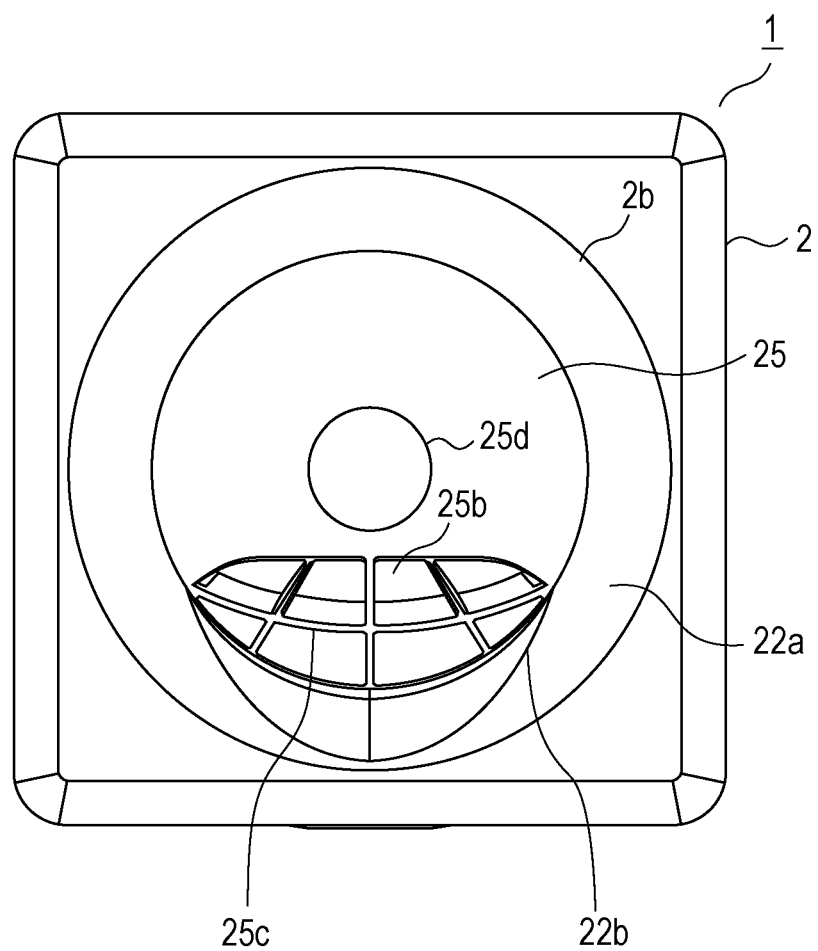
FIG. 12 is a top view illustrating the charged particle emission device of the first preferred embodiment of the present invention without the air directing plate.

FIG. 12 shows a top view of the housing 2 without the air directing plate 10. In the communication port 25b of the light guide plate 25, an air direction varying portion 25c that guides the air flow ascending the first blowing duct 21 forward is preferably provided in a lattice shape projecting downward.

A concave portion 22b located in the inner wall 22a is provided in the front portion of the second blowing duct 22. Along with the lower portion of the concave portion 22b being arranged along the communication port 25b, the upper portion is defined on the inside of the peripheral edge of the circular air outlet 2b. The inner surface of the concave portion 22b is defined by a conical surface defined as a straight line in which the cross-sectional surface perpendicular or substantially perpendicular to the air outlet 2b is inclined. The inner surface of the periphery of the concave portion 22b of the second blowing duct 22 preferably has a horn shape in which the cross-sectional shape perpendicular or substantially perpendicular to the air outlet 2b is defined as a convex curve inclined to the inside.

A width expander that widens the flow path between the lower surface 10a of the air directing plate 10 and the inner wall 22a of the second blowing duct 22 wider than the periphery is defined by the concave portion 22b. In so doing, it is possible for the flow rate of the air flow delivered forward from the outflow portion 8 to be increased. It is possible for the air flow delivered forward by the air direction varying portion 25c to be further increased.

In the charged particle emission device 1 of the above-described configuration, when the air outlet 2b is opened by the air directing plate 10 popping up, the blower fan 30, the ion generating element 40, and the LED 26 are driven. Dust in the air flow from the intake port 2a into the housing 2 is trapped by the filter 23, and is guided from the intake port 30b to the blower fan 30 by passing through the suction duct 23, as shown in the arrow A1. A portion of the air flow is guided from the intake port 30c to the blower fan 30 by flowing outside the duct member 32, as shown in by the arrow A2.

The air flow delivered from the exhaust port 30d of the blower fan 30 ascends the first blowing duct 21 as shown by the arrow B1 (refer to FIG. 5). At this time, ions generated by the ion generating element 40 are included in the air flow. The air flow including ions ascends as shown by the arrow B2 (refer to FIG. 5) by passing to the second blowing duct 22 via the communication port 25b, and is delivered radially from the outflow portion 8 as shown by the arrow B3.

At this time, along with the air flow passing from the communication port 25b located in the front portion of the housing 2 to the second blowing duct 22, the air flow is guided forward by the air direction varying portion 25c. The flow path width of the front portion between the second blowing duct 22 and the air directing plate 10 is widened by the concave portion 22b. In so doing, a large amount of air flow is delivered in a focused manner to the front of the charged particle emission device 1.

Accordingly, the air flow including a high concentration of ions is delivered to a user facing the front surface of the charged particle emission device 1. In so doing, it is possible to obtain a disinfecting effect in the vicinity of the user and a moisturizing effect for the skin of the user due to the ions along with providing the user with a pleasant cooling sensation. It is possible to diffuse ions in the room by the air flow including ions delivered to the side and the rear of the charged particle emission device 1, and to circulate the air along with performing disinfection and deodorizing of the periphery.

Light guided by the light guide plate 25 is emitted toward the air outlet 2b according to the driving of the LED 26, and is reflected radially by the lower surface 10a of the air directing plate 10. In so doing, it is possible to directly illuminate the periphery of the charged particle emission device 1. At this time, the light emitted from the front portion of the light guide plate 25 is reduced by the communication port 25b. Therefore, it is possible to reduce glare for the user facing the front surface of the charged particle emission device 1. Because the communication port 25b is located on the opposite side to the incident surface 25a with respect to the shaft portion 17, it is possible to further reduce the light emitted from the front portion of the light guide plate 25.

According to the present preferred embodiment, the communication port 25b of the first and second blowing ducts 21 and 22 is preferably biased toward the forward end portion (predetermined direction) with respect to the air outlet 2b. A concave portion 22b (width expander) is preferably configured such that the flow path widens at the front portion between the air directing plate 10 that guides the air flow radially by being located facing the air outlet 2a and the second blowing duct 22 wider than the periphery. In so doing, it is possible for ions to be diffused in the room by delivering the air flow including ions from the periphery along with being able to perform air blowing in a focused manner toward the user. Accordingly, it is possible to improve the convenience of operation of the charged particle emission device 1.

It is possible to easily realize a width expander that widens the flow path at the front portion between the air directing plate 10 and the second blowing duct 22 wider than the periphery with the concave portion 22b located in the inner wall 22a of the second blowing duct 22.

The cross-sectional shape of the inner surface of the concave portion 22b is preferably defined as an inclined straight line, and the cross-sectional shape of the inner surface of the periphery of the concave portion 22b is preferably defined in a convex curve which is inclined to the inside. In so doing, it is possible to widen the flow path between the air directing plate 10 and the second blowing duct with the concave portion 22 without providing a protrusion due to the concave portion 22 at the peripheral edge of the air outlet 2b. Accordingly, it is possible to improve the appearance of the charged particle emission device 1 by the circular or substantially circular air outlet 2b and the air directing plate 10. The planar shapes of the air directing plate 10 and the air outlet 2b may be the same or substantially the same polygonal shape, for example.

Since the air direction varying portion 25c that guides the airflow that passes through the first blowing duct 21 forward (predetermined direction) is provided in the communication port 25b, it is possible for the air flow delivered toward the user to be increased.

Because positive ions and negative ions are released by the ion generating element 40, it is possible to obtain a moisturizing effect for the skin of the user through the air flow with a high ion concentration delivered toward the user, along with obtaining a disinfecting effect and a deodorizing effect at the periphery.

A suction duct 20 that guides the air flow from the suction port 2a to the intake port 30b, and channels 50a and 50b (auxiliary suction path) that guide the air flow to the intake port 30c via the opening portion 32b facing the upper portion of the circuit board 34 are provided, and the air flow passes from a downward direction to an upward direction along the circuit board 34 in the channel 50b. In so doing, cooling is possible from the lower portion to the upper portion of the circuit board 34 by the air flow that ascends toward the opening portion 32b. Accordingly, it is possible to achieve size reductions in the air-blowing device 1 by reducing the heat dissipation space in the housing 2 of the circuit board 34.

The blower fan 30 is preferably configured as a double-face suction type fan that sucks in the air flow from both sides in the axial direction via a plurality of paths (20, 50a, 50b). Therefore, it is possible to deliver a uniform air flow by preventing a bias in the axial direction of the flow rate, along with improving the blowing efficiency compared to a single-face suction-type blower fan.

The opening portion 32b having a smaller opening area than the intake port 30c is opened at the step portion 32e located further toward the upper portion of the fan holding portion 32a (dividing wall) separated from the intake port 30c. In so doing, it is possible for the flow path of the lower portion of the channel 50b in which the air flow is warped and passes from the channel 50a to be secured to be wide. In addition, because the intake port 30c and the duct holding portion 32a are separated by the step portion 32e, it is possible to diffuse the air flow from the small diameter opening portion 32b, and guide the air flow to the large diameter intake port 30c. Accordingly, it is possible to further improve the blowing efficiency.

A chamfer 32c is preferably provided in the lower end of one side wall (rear surface side) that neighbors the duct holding portion 32a (divining wall) facing the suction port 2a, and the channel 50a (auxiliary suction path) is defined between the outer surface of the chamfer 32c and the housing 2. Accordingly, it is possible to easily realize a channel 50a that guides the air flow in the intake port 30c.

Since the pair of discharge electrodes 41 that release positive ions and negative ions to the first blowing duct 21 are preferably located in parallel or substantially in parallel in the axial direction of the blower fan 30, it is possible for positive ions and negative ions to be uniformly included in the air flow that passes uniformly in the axial direction. Accordingly, it is possible to improve the disinfecting effect and the deodorizing effect due to the delivery of ions.

Since the communication port 25b is defined in the light guide plate 25 biased with respect to the air outlet 2b, the light emitting area of the light guide plate 25 in the region in which the communication port 25b is defined is small compared to the light emitting area of the light guide plate 25 in other regions. In other words, since the light emission amount with respect to the air blowing direction is significantly reduced, the amount of glare is significantly reduced. In addition, light emitted from the light guide plate 25 is reflected in the delivery direction of the air flow by the air directing plate 10. In other words, the light emitted from the light guide plate 25 is reflected by the air directing plate 10, thus performing indirect illumination of the periphery of the air-blowing device 1. Accordingly, the amount of glare is significantly reduced since it is not easily directly viewed by the user.

Since the air direction varying portion 25c is preferably defined in the light guide plate 25, it is not necessary to provide the air direction varying portion 25c as a separate component. Accordingly, the size of the overall air-blowing device 1 does not increase.

The shaft portion 17 is interposed between the incident surface 25a and the communication port 25b. In other words, a portion of the light emitted from the LED 26 and guided by being incident from the incident surface 25a is blocked by the shaft portion 17. Accordingly, the luminance of the light guide plate 25 in the region in which the communication port 25b is defined becomes lower compared to the luminance of the light guide plate 25 in the other regions. Accordingly, the amount of glare is significantly reduced.

Since the LED 26 is lit if the air-blowing device 1 is in an operating state, and the LED 26 is turned off if in a stopped state, it is possible to easily determine the working state.

Second Preferred Embodiment

Figure 13:
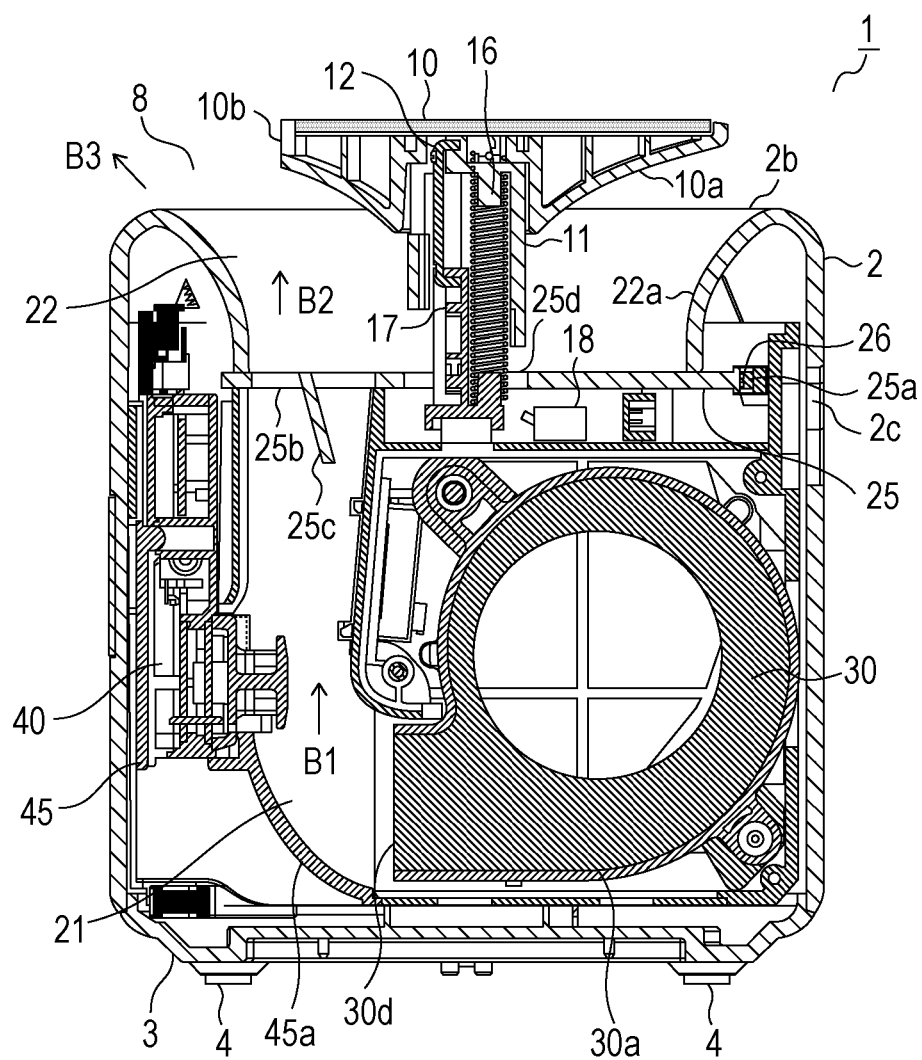
FIG. 13 is a right side cross-sectional view illustrating the charged particle emission device of a second preferred embodiment of the present invention.

Next, FIG. 13 shows a right side cross-sectional view illustrating the charged particle emission device 1 of the second preferred embodiment of the present invention. For convenience of description, the same elements as the first preferred embodiment shown in the above-described FIGS. 1 to 12 will be given the same reference numerals. The present preferred embodiment preferably does not include the concave portion 22b (refer to FIG. 12), and a notch portion 10b is preferably provided in the air directing plate 10. Other elements and configurations are preferably the same or substantially the same as the first preferred embodiment.

The planar shape of the air outlet 2b preferably has a circular or substantially circular shape. The air directing plate 10 covers the air outlet 2b, and a notch portion 10b in which a portion of the front portion is notched with respect to the circular shape with the same or substantially the same diameter as the air outlet 2b. A width expander that widens flow path between the lower surface 10a of the air directing plate 10 and the inner wall 22a of the second blowing duct 22 widens becomes wider than the periphery preferably includes the notch portion 10b. In so doing, it is possible for the flow rate of the air flow delivered forward from the outflow portion 8 to be increased.

According to the present preferred embodiment, similarly to the first preferred embodiment, the communication port 25b of the first and second blowing ducts 21 and 22 is biased to the forward end portion (predetermined direction) with respect to the air outlet 2b. A notch portion 10b (width expander) that widens the flow path at the front portion between the air directing plate 10 that guides the air flow radially by facing the air outlet 2a and the second blowing duct 22 wider than the periphery is provided. In so doing, it is possible for ions to be diffused in the room by delivering the air flow including ions from the periphery along with being able to perform air blowing in a focused manner toward the user. Accordingly, it is possible to improve the convenience of operation of the charged particle emission device 1.

It is possible to easily realize a width expander that widens the flow path at the front portion between the air directing plate 10 and the second blowing duct 22 wider than the periphery with the notch portion 10b in which a portion of the front of the air directing plate 10 is notched.

In the first and second preferred embodiments of the present invention, although the air flow including ions bonded with the water content in the air is delivered by the ion generating element 40 (charged particle generating element), other charged particles may be delivered. For example, charged particulate water may be delivered as the charged particles. Specifically, it is possible to create charged particulate water including a radical component with an electrostatic atomization apparatus. That is, condensed water occurs on the surface of the discharge electrodes according to the cooling or the like of the discharge electrodes provided in the electrostatic atomization apparatus by a Peltier device. When a negative high voltage is applied to the discharge electrodes, charged particulate water is generated from the condensed water.

Preferred embodiments of the present invention and modifications thereof are able to be used as a charged particle emission device that delivers charged particles, such as ions.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A charged particle emission device, comprising:
a housing including a suction port and an air outlet;
a blower fan in the housing;
a first blowing duct on an exhaust side of the blower fan;
a second blowing duct in which an air outlet is opened at one end and configured to communicate with the first blowing duct via a communication port;
a charged particle generating element configured to release charged particles in the first blowing duct;
a wind direction plate configured to radially guide an air flow and located opposite to the air outlet; and
a width expander configured such that the communication port is biased with respect to the one end in a predetermined direction with respect to the air outlet, and configured such that the width expander widens a flow path between the second blowing duct and the air directing plate on the one end wider than a periphery.

2. The charged particle emission device according to claim 1, wherein the width expander includes a concave portion provided in an inner wall of the second blowing duct.

3. The charged particle emission device according to claim 2, wherein the flow path widens as the second blowing duct progresses toward the air outlet, and a cross-sectional shape of an inner surface of the concave portion perpendicular or substantially perpendicular to the air outlet defines an inclined straight line and the cross-sectional shape of the inner surface of an area around the concave portion perpendicular or substantially perpendicular to the air outlet defines a convex curve which is inclined relative to an inside.

4. The charged particle emission device according to claim 1, wherein the width expander includes a notch portion extending in a predetermined direction in the air directing plate.

5. The charged particle emission device according to claim 1, further comprising an air direction varying portion provided at the communication port and configured to guide an air flow passing through the first blowing duct in a predetermined direction.

6. The charged particle emission device according to claim 1, wherein the charged particles include positive ions and negative ions.

* * * * *